(12) United States Patent
Schellens

(10) Patent No.: US 6,469,022 B1
(45) Date of Patent: Oct. 22, 2002

(54) METHOD, COMPOSITIONS AND KITS FOR INCREASING THE ORAL BIOAVAILABILITY OF PHARMACEUTICAL AGENTS

(75) Inventor: Jan H. M. Schellens, Amsterdam (NL)

(73) Assignee: Smith Kline Beecham, Corporation, Philadelphia, PA (US)

( * ) Notice: Subject to any disclaimer, the term of this patent is extended or adjusted under 35 U.S.C. 154(b) by 0 days.

(21) Appl. No.: 09/486,938

(22) PCT Filed: Sep. 3, 1998

(86) PCT No.: PCT/EP98/05557

§ 371 (c)(1),
(2), (4) Date: Aug. 17, 2000

(87) PCT Pub. No.: WO99/12570

PCT Pub. Date: Mar. 18, 1999

(30) Foreign Application Priority Data

Sep. 5, 1997 (GB) ............................................. 9718903

(51) Int. Cl.⁷ ........................ A61K 31/44; A61K 31/335
(52) U.S. Cl. ....................................... 514/297; 514/449
(58) Field of Search .................................. 514/297, 449

(56) References Cited

U.S. PATENT DOCUMENTS 5,604,237 A    2/1997    Dumaitre et al.

FOREIGN PATENT DOCUMENTS

| EP | 0 494 623 A | 7/1992 |
| WO | WO 97 15269 A | 5/1997 |
| WO | WO 98 53811 A | 12/1998 |

OTHER PUBLICATIONS

Hyafil, F., et al, "In Vitro and In Vivo Reversal Of Multidrug Resistance By GF120918, An Acridonecarboxamide Derivative" Cancer Research, vol. 53, No. 1, Oct. 1, 1993, pp. 4595–4602.

Sparreboom, A. et al, "Limited Oral Bioavailability And Active Epithelial Excretion Of Paclitaxel (Taxol) Caused By P–glycoprotein In the Intestine", Proc. Natl. Acad. Sci, USA, vol. 94, Mar. 1997, pp. 2031–2035.

Sikic B.I., et al, "Modulation and Prevention Of Multidrug Resistance By Inhibitors Of P–glycoprotein", Cancer Chemotherapy and Pharmacology, Supplement, 40/–, (S13–S19), 1997.

*Primary Examiner*—Jerome D. Goldberg
(74) *Attorney, Agent, or Firm*—John L. Lemanowicz

(57) ABSTRACT

A combination of 9,10-dihydro-5-methoxy-9-oxo-N-[4-[2-(1,2,3,4-tetrahydro-6,7,-dimethoxy-2-isoquinolinyl)ethyl]phenyl]-4-acridinecarboxamide or a salt thereof and paclitaxel and its analogs or derivatives.

1 Claim, 1 Drawing Sheet

Figure 1:
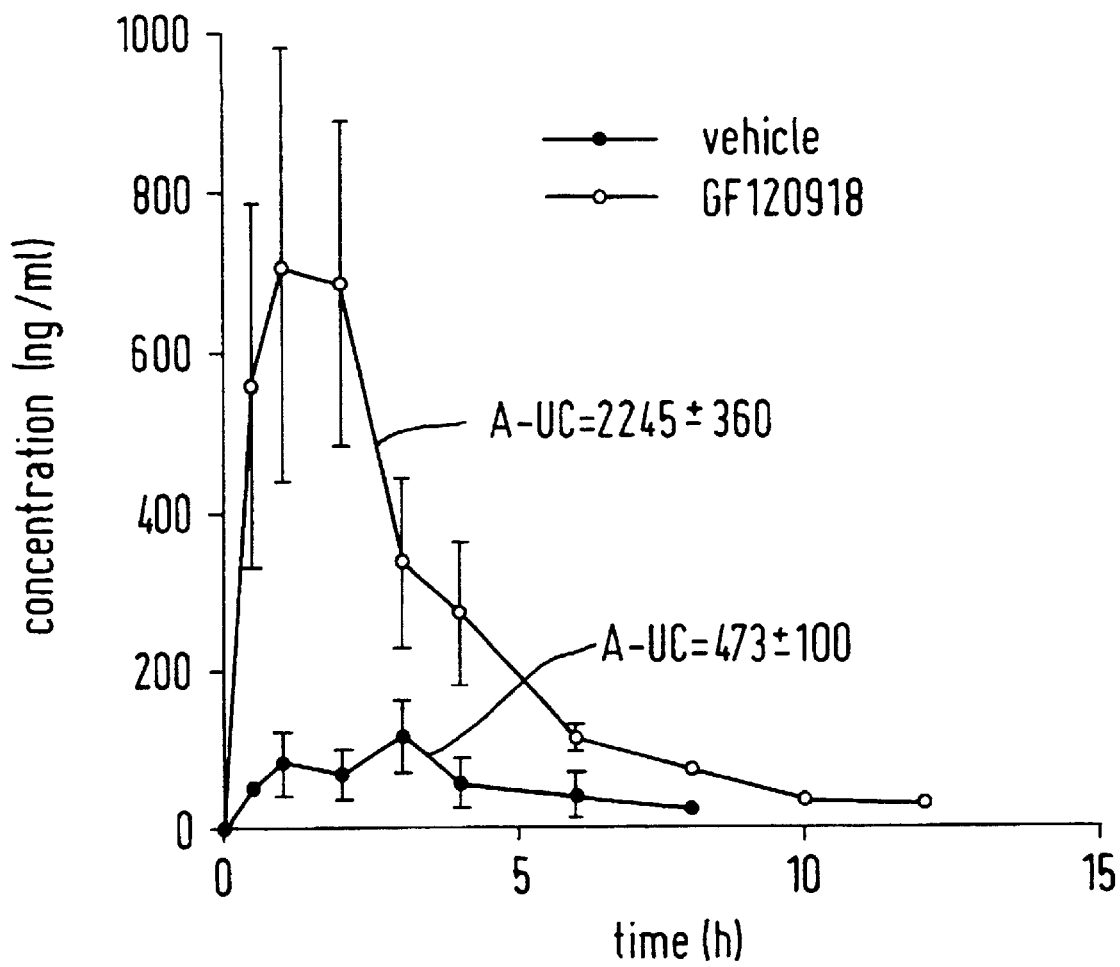

METHOD, COMPOSITIONS AND KITS FOR INCREASING THE ORAL BIOAVAILABILITY OF PHARMACEUTICAL AGENTS

This application is filed pursuant to 35 U.S.C. §371 as a United States National Phase Application of International Application No. PCT/EP98/05557 filed Sep. 3, 1998, which claims priority from both GB 9718903.9 filed Sep. 5, 1997.

The invention relates to methods, compositions and kits for improving the oral bioavailability of pharmaceutical agents that are poorly absorbed from the gastrointestinal tract, and to methods of treatment of patients through the oral administration of such agents. One aspect of the invention relates to the use of 9,10-dihydro-5-methoxy-9-oxo-N-[4-[2-(1,2,3,4-tetrahydro-6,7-dimethoxy-2-isoquinolinyl) ethyl]phenyl]-4-acridinecarboxamide and physiologically acceptable salts and solvates thereof to enhance the oral bioavailability of paclitaxel and related taxanes.

Many valuable pharmacologically active compounds cannot be effectively administered by the oral route because of poor systemic absorption from the gastrointestinal tract. All these pharmaceutical agents are, therefore, generally administered via intravenous or intramuscular routes, requiring intervention by a physician or other health care professional, entailing considerable discomfort and potential local trauma to the patient and even requiring administration in a hospital setting with surgical access in the case of certain IV infusions.

It has been speculated that, in some cases, the poor bioavailability of a drug after oral administration is a result of the activity of a multidrug transporter, a membrane-bound P-glycoprotein, which functions as an energy-dependent transport or efflux pump to decrease intracellular accumulation of drug by extruding xenobiotics from the cell. This P-glycoprotein has been identified in normal tissues of secretory endothelium, such as the biliary lining, brush border of the proximal tubule in the kidney and luminal surface of the intestine, and vascular endothelial cells lining the blood brain barrier, placenta and testis.

It is believed that the P-glycoprotein efflux pump prevents certain pharmaceutical compounds from transversing the mucosal cells of the small intestine and, therefore, from being absorbed into the systemic circulation. A number of known non-cytotoxic pharmacological agents have been shown to inhibit P-glycoprotein, including cyclosporin A (also known as cyclosporine), verapamil, tamoxifen, quinidine and phenothiazines, among others. Many of these studies were aimed at achieving greater accumulation of cytotoxic drugs inside tumour cells. In fact, clinical trials have been conducted to study the effects of cyclosporine on the pharmacokinetics and toxicities of paclitaxel (Fisher et al., *Proc. Am. Soc. Clin, Oncol.*, 13: 143, 1994); doxorubicin (Bartlett et al., *J. Clin, Onc*—12:835–842, 1994); and etoposide (Lum et al., *J. Clin, Onc*, 10:1635–42, 1992), all of which are anti-cancer agents known to be subject to multidrug resistance (MDR). These trials showed that patients receiving intravenous cyclosporine prior to or together with the anti-cancer drugs had higher blood levels of those drugs, presumably through reduced body clearance, and exhibited the expected toxicity at substantially lower dosage levels. These findings tended to indicate that the concomitant administration of cyclosporine suppressed the MDR action of P-glycoprotein, enabling larger intracellular accumulations of the therapeutic agents. For a general discussion of the pharmacologic implications for the clinical use of P-glycoprotein inhibitors, see Lum et al., *Drug Resist, Clin, Onc, Hemat.*, 9: 319–336 (1995); Schinkel et al., *Eur, J. Cancer*, 31A: 1295–1298 (1995).

In the aforedescribed studies relating to the use of cyclosporine to increase the blood levels of pharmaceutical agents subject to P-glycoprotein mediated resistance, the active agents and the cyclosporine were administered intravenously. No suggestion was made in these publications that cyclosporine or other substances believed to inhibit the P-glycoprotein efflux pump could be orally administered to substantially increase the bioavailability of orally administered anti-cancer drugs and other pharmaceutical agents which are themselves poorly absorbed from the gut without producing highly toxic side effects. Indeed, in the 1995 review paper cited above, Lum et al. showed that concomitant IV administration of MDR inhibitors and chemotherapeutic agents subject to MDR increased toxicity levels and exacerbated the patients' serious side effects. Schinkel et al. briefly adverted to the fact that MDR 1 and P-glycoprotein are abundant in the mucosal cells of the intestine, and that this may affect the oral bioavailability of P-glycoprotein substrate drugs, but did not suggest or imply that the oral administration of MDR suppressing agents could improve the bioavailability of the orally unavailable agents. Furthermore, like Lum et al., Schinkel et al. warned that P-glycoprotein inhibitors can dramatically increase toxicity in chemotherapy patients and should, therefore, be used cautiously.

In an earlier publication, Schinkel et al. showed that absorption of orally ingested ivermectin was increased in mice homozygous for a disruption of the MDR1 a gene in comparison with normal mice, demonstrating that P-glycoprotein played a major role in reducing the bioavailability of this agent (*Cell* 77: 491–502, 1994). In addition, this study also showed that the penetration of vinblastine into various tissues was enhanced in the mutant mice. A more recent publication by Sparreboom et al. (*Proc. Natl. Acad. Sci. USA* 94: 2031–2035, 1997) confirms these studies by showing that uptake of oral taxol is increased in these mice.

None of the published studies provided any regimen for implementing the effective oral administration of otherwise poorly bioavailable drugs, e.g., indicating the respective dosage ranges and timing of administration for specific target drugs and bioavailability-enhancing agents (bioenhancers) or demonstrating which MDR-inhibiting agents are best suited for promoting oral absorption of each target drug or class of drugs.

Methods disclosed in the art for increasing gut absorption of drugs that have until now only been administered parenterally generally focus on the use of permeation and solubility enhancers as promoting agents, or the co-administration by intraluminal perfusion in the small intestine or by the intravenous route of P-glycoprotein inhibitors, e.g., Leu et al., *Cancer Chemother, Pharmacol.*, 35: 432–436, 1995 (perfusion or IV infusion of quinidine suppresses efflux of etoposide into the lumen of the G.I. tract from the blood). But these methods suffer from numerous drawbacks. The solubility and permeability enhancing agents are often either impractical or ineffective for oral administration in the doses required and may interfere with the pharmacological activity of the target drug and/or other drugs given in combination with the target drug. Parenteral administration of P-glycoprotein inhibitors in therapeutic (or near-therapeutic) doses into humans can cause severe clinical consequences. In the case of quinidine, for example, IV administration may cause arrhythmias, peripheral vasodilation, gastrointestinal upset and the like.

In published PCT application WO 95/20980 (published Aug. 10, 1995) Benet et al disclose a purported method for increasing the bioavailability of orally administered hydrophobic pharmaceutical compounds. This method comprises orally administering such compounds to the patient concurrently with a bioenhancer comprising an inhibitor of a cytochrome P450 3A enzyme or an inhibitor of P-glycoprotein-mediated membrane transport. Benet et al., however, provide virtually no means for identifying which bioavailability enhancing agents will improve the availability of specific "target" pharmaceutical compounds, nor do they indicate specific dosage amounts, schedules or regimens for administration of the enhancing or target agents. In fact, although the Benet application lists dozens of potential enhancers (P450 3A inhibitors) and target drugs (P450 3A substrates), the only combination of enhancer and target agent supported by any experimental evidence in the application is ketoconazole as the enhancer and cyclosporin A as the target drug.

Thus, a need for a safe and effective method for increasing the systemic availability upon oral administration of drugs that are administered parenterally still exists. Current administration of such drugs is limited to the parenteral route because they are not absorbed sufficiently or consistently when administered by the oral route.

In published PCT application WO97/15269 (published May 1, 1997) Broder et al teach that the combination of paclitaxel with cyclosporine orally achieves comparable local tissue concentrations to paclitaxel administered via the intravenous route. Moreover, WO97/15269 teaches that ketoconazole has significant oral bioavailability—enhancing activity whilst other MDR inhibitors such as verapamil, dipyridamole and megestrol have less enhancing activity and progesterone even has none. Broder et al thus teaches that only certain P-glycoprotein inhibitors increase oral bioavailability. Moreover, the two most successful bioenhancers, cyclosporine and ketoconazole both interact with P450 3A.

It has now been discovered that, surprisingly, 9,10-dihydro-5-methoxy-9-oxo-N-[4-[2-(1,2,3,4-tetrahydro-6,7-dimethoxy-2-isoquinolinyl)ethyl]phenyl]-4-acridinecarboxamide or a salt thereof, especially, its hydrochloride salt, can be used to substantially increase the oral bioavailability of the otherwise poorly available paclitaxel as well as its analogs and derivatives, preferably of compounds of formula I

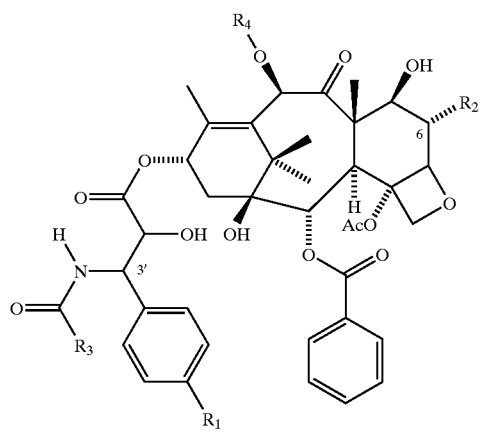

(I)

wherein $R_1$ and $R_2$ is hydrogen or hydroxy, $R_3$ is phenyl (Ph) or $OC(CH_3)_3$ and $R_4$ is $CH_3CO$ (acetyl (Ac)) or hydrogen. 9,10-dihydro-5-methoxy-9-oxo-N-[4-[2-(1,2,3,4-tetrahydro-6,7,-dimethoxy-2-isoquinolinyl)ethyl]pheny]-4-acridinecarboxamide is a P-glycoprotein inhibitor but does not inhibit with the cytochrome P-450 system.

Accordingly, the present invention relates to the use of 9,10-dihydro-5-methoxy-9-oxo-N-[4-[2-(1,2,3,4-tetrahydro-6,7,-dimethoxy-2-isoquinolinyl)ethyl]pheny]-4-acridinecarboxamide or a salt thereof for the manufacture of a medicament for use in increasing the bioavailability of paclitaxel or an analog or derivative thereof. Such use would be carried out by oral administration of paclitaxel or an analog or derivative thereof (the active agent) together with said bioenhancer (9,10-dihydro-5-methoxy-9-oxo-N-[4-[2-(1,2,3,4-tetrahydro-6,7,-dimethoxy-2-isoquinolinyl)ethyl]pheny]-4-acridinecarboxamide).

Taxanes with anti-cancer activity are also included as active agents in accordance with the present invention.

The present invention relates in another aspect to a method of increasing the oral bioavailability of pharmaceutical agents that are poorly absorbed or not absorbed at all from the gastrointestinal tract or gut by pre-administering and/or simultaneously administering to a subject by the oral route one or a combination of agents known to be effective in inhibiting the P-glycoprotein drug transport pump. If pre-administration is used, the bioavailability enhancing agent or agents must be administered in sufficient quantities and within a short enough time period before administration of the drug whose bioavailability is to be increased (the "target drug" or "target agent") so that a sufficient level of the enhancing agent remains at the site of absorption at the time of administration of the target agent to effectively inhibit the activity of the P-glycoprotein or other multi-drug transporter substances. 9, 10-dihydro-5-methoxy-9-oxo-N-[4-[2-(1,2,3,4-tetrahydro-6,7,-dimethoxy-2-isoquinolinyl)ethyl]pheny]-4-acridinecarboxamide itself has very poor bioavailability across the gut making it a particularly good bioenhancer as it remains at the site of absorption to effectively inhibit the activity of the P-glycoprotein.

In a further aspect, the invention pertains to compositions or dosage forms for oral administration of pharmaceutical agents that were heretofore available for parenteral administration only. A fourth aspect of the invention relates to the administration of such oral dosage forms or a combination thereof to patients for treatment of diseases responsive to taxol and derivatives or analogs thereof which are contained therein.

The invention also pertains to pharmaceutical kits comprising one or more oral dosage forms containing as the target agent taxol and derivatives or analogs thereof and one or more oral dosage forms containing as the enhancing agent, 9,10-dihydro-5-methoxy-9-oxo-N-[4-[2-(1,2,3,4-tetrahydro-6,7,-dimethoxy-2-isoquinolinyl)ethyl]pheny]-4-acridinecarboxamide The present invention pertains generally to increasing the oral absorption and bioavailability upon oral administration of pharmacologically active agents, particularly agents that are poorly absorbed or not absorbed at all from the gastrointestinal tract or gut. The preferred embodiments of the invention pertain to (a) a method for increasing the oral bioavailability of antitumour agents, in particular paclitaxel (currently marketed as TAXOL® by Bristol-Myers Squibb Oncology Division) and its derivatives; other taxanes which exhibit antitumour activity; the semi-synthetic paclitaxel analog docetaxel (N-debenzoyl-N-tert-butoxycarbonyl-10-deacetyl paclitaxel), produced under the trademark TAXOTERE® by Rhone-Poulenc Rorer S.A; (b) dosage forms and kits for oral administration of antitumour agents and other drugs heretofore administered only parenterally; and (c) methods of treatment of cancer patients with such oral dosage forms or combinations thereof.

The phrases "oral bioavailability" and "bioavailability upon oral administration" as used herein refer to the systemic availability (i.e., blood/plasma levels) of a given amount of drug administered orally to a patient.

The term bioenhancer (or enhancing agent) as used herein refers to a compound which enhances and thus increases the oral bioavailability of a compound which normally has poor oral bioavailability. The compound whose oral bioavailability is to be enhanced is referred to as the active (or target) agent/drug. The bioenhancer (enhancing agent) of the present invention is 9, 10-dihydro-5-methoxy-9-oxo-N-[4-[2-(1,2,3,4-tetrahydro-6,7,-dimethoxy-2-isoquinolinyl) ethyl]phenyl]-4-acridinecarboxamide whilst the active agent (target agent/drug) of the present invention is paclitaxel and its derivatives or analogs.

Paclitaxel [2aR-[2aα,4,β,4aβ,6β,9α(αR*,βS*),-11α,12α, 12aα,12bα]]-β-(Benzoylamino)-α-(hydroxybenzenepropanoic acid 6,12b-bis(acetyloxy)-12-(benzoloxy)-2a,3, 4,-4a,5,6,9,10,11,12,12a,12b-dodecahydro-4,11-dihydroxy-4a,8,-13,13-tetramethyl-5-oxo-7,11-methano-1H-cyclodeca [3,4]benz-[1,2-b]oxet-9-yl ester; 5β,20-epoxy-1,2α,4,7β, 10β,13α-hexa-hydroxytax-11-en-9-one 4,10-diacetate 2-benzoate 13-ester with (2R,3S)-N-benzoyl-3-phenylisoserine; is a natural diterpene product isolated from the Pacific yew tree Taxus brevifolia). It is a member of the taxane family of terpenes. It was first isolated in 1971 by Wani et al. *J. Am. Chem, Soc.,* 93:2325. 1971), who characterized its structure by chemical and X-ray crystallographic methods. One mechanism for its activity relates to paclitaxel's capacity to bind tubulin, thereby inhibiting cancer cell growth. Schiff et al., *Proc. Natl, Acad, Sci. USA,* 77:1561–1565 (1980); Schiff et al., *Nature,* 277:665–667 (1979); Kumar, *J. Biol, Chem,* 256: 10435–10441 (1981). For a review of synthesis and anticancer activity of some paclitaxel derivatives see: D. G. I. Kingston et al., Studies in Organic Chemistry vol. 26, entitled "New trends in Natural Products Chemistry 1986", Attaur-Rahman, P. W. Le Quesne, Eds. (Elsevier, Amsterdam, 1986) pp 219–235.

Paclitaxel has been approved for clinical use in the treatment of refractory ovarian cancer in the United States (Markman et al., *Yale Journal of Biology and Medicine,* 64:583, 1991; McGuire et al., *Ann. Intem, Med.,* 111:273, 1989). It is effective for chemotherapy for several types of neoplasms including breast (Holmes et al., *J. Nat, Cancer Inst,* 83:1797, 1991) and has been approved for treatment of breast cancer as well. It is a potential candidate for treatment of neoplasms in the skin (Einzig et al., *Proc. Am. Soc. Clin, Oncol.,* 20:46) and head and neck carcinomas (Forastire et al. *Sem, Oncol,* 20:56, 1990). The compound also shows potential for the treatment of polycystic kidney disease (Woo et al., *Nature,* 368:750. 1994), lung cancer and malaria.

Paclitaxel is only slightly soluble in water and this has created significant problems in developing suitable injectable and infusion formulations useful for anticancer chemotherapy. Some formulations of paclitaxel for IV infusion have been developed utilizing CREMOPHOR EL™ (polyethoxylated castor oil) as the drug carrier because of paclitaxel's aqueous insolubility. For example, paclitaxel used in clinical testing under the NCI has been formulated in 50% CREMOPHOR EL™ and 50% dehydrated alcohol. CREMOPHOR EL™ however, when administered intravenously, is itself toxic and produces vasodilation, laboured breathing, lethargy, hypotension and death in dogs. It is also believed to be responsible for the allergic-type reactions observed during paclitaxel administration.

In an attempt to increase paclitaxel's solubility and to develop more safe clinical formulations, studies have been directed to synthesizing paclitaxel analogs where the 2' and/or 7-position is derivatized with groups that would enhance water solubility. These efforts have yielded prodrug compounds that are more water soluble than the parent compound and that display the cytotoxic properties upon activation. One important group of such prodrugs includes the 2'-onium salts of paclitaxel and docetaxel, particularly the 2'-methyipyridinium mesylate (2'-MPM) salts.

Paclitaxel is very poorly absorbed when administered orally (less than 1%); see Eiseman et al., *Second NCI Workshop on Taxol and Taxus* (September 1992); Stuffness et al. in *Taxol Science and Applications* (CRC Press 1995). Eiseman et al. indicate that paclitaxel has a bioavailability of 0% upon oral administration, and Stuffness et al. report that oral dosing with paclitaxel did not seem possible since no evidence of antitumour activity was found on oral administration up to 160 mg/kg/day. Moreover, no effective method has been developed to enable the effective administration of oral paclitaxel (i.e., a method of increasing the oral bioavailability of paclitaxel) or of other oral taxanes or paclitaxel analogs such as docetaxel which exhibit antitumour activity. For this reason, paclitaxel has not until now been administered orally to human patients, and certainly not in the course of treating paclitaxel-responsive diseases.

Docetaxel 2aR-[2aα,4β,4aβ,6β,9α(αR*,βS),-11α,12α, 12aα,12bα]]-β-[[(1,1-Dimethylethoxy)carbonyl]-amino]-α-hydroxybenzenepropanoic acid 12b-(acetyloxy)-12-(benzoloxy)-2a,3,4,-4a,5,6,9,10,11,12,12a,12b-dodecahydro-4,6,11trihydroxy-4a,8,-13,13-tetramethyl-5-oxo-7,11-methano-1H-cyclodeca[3,4]benz-[1,2-b]oxet-9-yl ester; N-debenzoyl-N-(tert-butoxycarbonyl)-10-deacetyltaxol has become commercially available as TAXOTERE® in parenteral form for the treatment of breast cancer. To date no reference has been made in the scientific literature to oral absorption of docetaxel in animals or patients. Docetaxel is a semisynthetic derivative of paclitaxel q.v., prepared using a natural precursor, 10-deacetyl-baccatin III, extracted from the needle of the European Yew tree.

9,10-dihydro-5-methoxy-9-oxo-N-[4-[2-(1,2,3,4-tetrahydro-6,7-dimethoxy-2-isoquinolinyl)ethyl]phenyl]-4-acridinecarboxamide and its synthesis is disclosed in granted European Patent No. 0569380—derived from PCT application WO92/12132.

It has now been discovered that paclitaxel and related taxanes with poor oral absorption profiles can be effectively administered orally with sufficient systemic absorption to exhibit therapeutic activity levels when said agents are co-administered orally with, an oral dose of 9,10-dihydro-5-methoxy-9-oxo-N-[4-[2-(1,2,3,4-tetrahydro-6,7-dimethoxy-2-isoquinolinyl)ethyl]phenyl]-4-acridinecarboxamide and it salts known to inhibit the multidrug resistance, drug transport activity of the P-glycoprotein intracellular pump.

The method of the invention for increasing the oral bioavailability of a paclitaxel and related taxanes with poor oral bioavailability of less than 10% comprises the oral administration of an oral absorption or bioavailability enhancing agent to a mammalian patient (human or animal) simultaneously with, or prior to, or both simultaneously with and prior to the oral administration to increase the quantity and duration of absorption of the intact target agent into the bloodstream.

The orally administered enhancing agents which may be used in accordance with the invention is 9,10-dihydro-5-methoxy-9-oxo-N-[4-[2-(1,2,3,4-tetrahydro-6,7-dimethoxy-2-isoquinolinyl)ethyl]phenyl]-4-acridinecarboxamide or a salt thereof. The most preferred salt is the hydrochloride salt.

The class of orally administered target therapeutic agents whose oral absorption is increased by the enhancing agents includes, but is not limited to, the following;

Paclitaxel, other taxanes, docetaxel and derivatives and prodrugs of all the foregoing, particularly their 2'-MPM salts and other 2'-methylpyridinium salts.

The dosage range of the enhancing agent to be co-administered with the target agent in accordance with the invention is about 0.1 to about 150 mg/kg preferably, from 5 to 50 mg/kg of patient body weight. More preferably 10 to 30 mg/kg and most preferably about 20 to 30 mg/kg. "Co-administration" of the enhancing agent comprehends administration substantially simultaneously with the target agent (either less than 1 hour before, preferably less than 0.5 hr. before, less than 0.5 hr. after or together), from about 0.5 to about 24 hr. before the administration of the target agent, or both, i.e., with one or more doses of the same or different enhancing agents given at least 0.5 hr. before and one dose given substantially simultaneously with (either together with or immediately before or after) the target agent. Additionally, "co-administration" comprehends administering more than one dose of target agent within 24 hrs after a dose of enhancing agent, in other words, the enhancing agent(s) need not be administered again before or with every administration of target agent, but may be administered intermittently during the course of treatment.

The dosage range of orally administered target agents will vary from drug to drug based on its therapeutic index, the requirements of the condition being treated, the status of the subject and so forth. The method of the invention makes it possible to administer paclitaxel and derivatives or analogs thereof orally ranging from about 20 mg/M$^2$ to about 1000 mg/m$^2$ (based on patient body surface area) or about 0.5–30 mg/kg (based on patient body weight) preferably 2 to 20 mg/kg and most preferably 5 to 10 mg/kg as single or divided (2–3) daily doses, and maintain the plasma levels of paclitaxel in humans in the range of 10–500 ng/ml preferably 20 to 500 ng/ml for extended periods of time (e.g., 8–12 hours) after each oral dose.

These levels are at least comparable to those achieved with 96 hour IV infusion taxol therapy (which causes the patient great inconvenience, discomfort, loss of time, infection potential, etc.). Moreover, such plasma levels of paclitaxel are more than sufficient to provide the desired pharmacological activities of the target drug, e.g., inhibition of tubulin disassembly (which occurs at levels of about 0.1 $\mu$M, or about 85 ng/ml) and inhibition of protein isoprenylation (which occurs at levels of about 0.03 $\mu$M, or about 25 ng/ml) which are directly related to its antitumour effects by inhibiting oncogene functions and other signal-transducing proteins that play a pivotal role in cell growth regulation.

It may be suitable in some instances to administer to the subject a higher initial loading dose of the target agent to achieve peak blood levels, followed by lower maintenance doses.

Two or more different enhancing agents and/or two or more different target agents may be administered together, alternately or intermittently in all of the various aspects of the method of the invention. The present invention also comprehends methods of treating mammalian patients afflicted with cancers, tumours, Kaposi's sarcoma, malignancies, uncontrolled tissue or cellular proliferation secondary to tissue injury, and any other disease conditions responsive to paclitaxel, taxanes, docetaxel, prodrugs and derivatives of all the foregoing, paclitaxel 2'-MPM, and docetaxel 2'-MPM with orally administered dosage forms comprising one or more of those agents. Among the types of carcinoma which may be treated particularly effectively with oral paclitaxel, docetaxel, other taxanes, and their prodrugs and derivatives, are hepatocellular carcinoma and liver metastases, and cancers of the gastrointestinal tract, pancreas and lung. Examples of non-cancerous disease conditions which may be effectively treated with these active agents administered orally in accordance with the present invention are uncontrolled tissue or cellular proliferation secondary to tissue injury, polycystic kidney disease and malaria. including chloroquine- and pyrimethamine-resistant malaria parasites (Pouvelle et al., J. Clin, Invest., 44: 413–417, 1994).

The antitumour agents which heretofore were administered only parenterally can now be administered in accordance with the invention by the oral route with sufficient bioavailability to provide pharmacologically active blood concentrations which will be particularly effective in the treatment of patients with primary tumours and metastases. Steady state plasma levels of Paclitaxel may be achieved upon oral co-administration with the enhancing agent of the invention within the first week of the regime, preferably within the first five days and most preferably within the first three days of the regimen. The levels of the target agent achieved at steady state are comparable to those achieved in patients by a 96-hour IV infusion of paclitaxel.

Oral bioavailability of paclitaxel and its analogs/derivatives ad ministered with 9,10-dihydro-5-methoxy-9-oxo-N[4-2-(1,2,3,4-tetrahydro-6,7-dimethoxy-2-isoquinolinyl)ethyl]phenyl]-4-acridinecarboxamide and/or its salts is more than 20%, preferably more than 25%, more preferably more than 30% and most preferably more than 50%. A range of 20 to 200% oral bioavailability is achieved, preferably between 30 to 100% and most preferably between 40 to 75%.

Maximum plasma concentration achieved may be more than 5 fold higher, preferably about 10 fold higher when paclitaxel and/or its analogs/derivatives are administered orally in combination with the bioenhancer of the present invention. A 27% response rate was found in taxane-failure patients with metastatic breast cancer treated with a continuous 96-hour infusion every three weeks (Seidman et al., J. Clin, Oncol.,14:1877, 1996). It is believed that similar results can be achieved with the treatment methods of the present invention, without the discomfort, inconvenience and risks of prolonged IV infusions.

Furthermore, and quite significantly, the elimination-phase concentration in the blood of paclitaxel when administered orally as provided herein, is approximately equal to that achieved with IV administration, and these high, therapeutically effective levels, can be maintained for as long as 8–12 hours after each administration.

Oral dosage forms of the target agents whose bioavailability is increased by the co-administration of the enhancing agents may be in the form of conventional tablets, capsules, caplets, gelcaps, pills, liquids (e.g., solutions, suspensions or elixirs), lozenges and any other oral dosage forms known in the pharmaceutical arts. The liquid preparations may include, for example, paclitaxel or other taxane in a vehicle comprising CREMOPHOR EL or other polythoxylated castor oil, alcohol and/or a polythoxylated sorbitan mono-oleate (e.g., TWEEN® 80, ICI Americas, Inc.). Each dosage form includes an effective amount of a target agent (for example, effective antitumour or antineoplastic amounts of an antitumour or antineoplastic agent) and pharmaceutically inert ingredients, e.g., conventional excipients, vehicles, fillers, binders, disentegrants, solvents, solubilizing agents, sweeteners, coloring agents and any other inactive ingredients which are regularly included in pharmaceutical dosage forms for oral administration. Many such dosage forms and oral vehicles immediately after listings of inactive ingredients therefor are set forth in *Remington's Pharmaceutical Sciences,* 17th edition (1985). Each dosage form also contains a pharmacologically effective amount, for example, an effective antineoplastic or tumour-reducing amount, of one of the target drugs.

Precise amounts of each of the target drugs in the oral dosage forms will vary depending on the age, weight, disease and condition of the patient. For example, paclitaxel dosage forms may contain sufficient quantities of paclitaxel to provide a daily dosage of about 20–1000 mg/m$^2$ (based on patient body surface area) or about 2–30 mg/kg (based on patient body weight) as single or divided (2–3) daily doses.

In establishing a treatment regimen for a particular patient treated with the oral, target drug-containing dosage forms of the invention, it is necessary to take into account the increased bioavailability provided by the concomitant/or prior oral administration of the enhancing agents.

Dosing schedules for the treatment method of the present invention, for example, the treatment of paclitaxel-responsive diseases with oral paclitaxel dosage forms co-administered with enhancing agents, can likewise be adjusted to account for the patient's characteristics and disease status. Preferred dosing schedules for administration of oral paclitaxel are (a) the daily administration to a patient in need thereof of 1–3 equally divided doses providing about 20–1000 mg/m$^2$ (based on body surface area), with said daily administration being continued for 1–4 consecutive days each 2–3 weeks, or (b) administration for about one day each week. The former schedule is comparable to use of a 96-paclitaxel infusion every 2–3 weeks, which is considered by some a preferred IV treatment regimen.

Oral administration of powerful chemotherapeutic agents in accordance with the invention may actually decrease toxic side effects in many cases as compared with currently utilized IV therapy. Rather than producing a sudden and rapid high concentration in blood levels as is usually the case with an IV infusion, absorption of the active agent through the gut wall (promoted by the enhancing agents), provides a more gradual appearance in the blood levels and a stable, steady-state maintenance of those levels at or close to the ideal range for a long period of time.

Pursuant to another aspect of the invention, combination oral dosage forms are provided which contain fixed quantities of at least one enhancing agent and at least one target agent. For example, such dosage forms can consist of tablets, capsules, caplets, gelcaps, pills, liquids, lozenges and any other conventional oral dosage forms containing as active ingredients an effective oral bioavailability enhancing amount of an antitumour or anti-neoplastic agent, as well as suitable inactive ingredients. One such combination product includes from about 0.5 to about 15 mg/kg of the active bioenhancer of the present invention together with about 20 to about 1000 mg/m$^2$ (based on average patient body surface area) of paclitaxel, docetaxel, other taxanes or paclitaxel or docetaxel derivatives such as paclitaxel 2-MPM or docetaxel 2'-MPM.

The co-administration of enhancing agents with the target drugs promotes not only the oral bioavailability of those agents but also enables their use in the treatment of tumours at sites highly protected by MDR, e.g., the testes and the brain. Another aspect of the present invention is, thus, a method of delivering antitumour drugs to tumour sites protected by MDR through the oral co-administration of enhancing agents and the antitumour agents, making it possible to treat brain tumours such as glioblastoma multiforme.

Yet another aspect of the present invention is a method of delivering an active paclitaxel metabolite to a disease site at therapeutic levels to treat paclitaxel responsive diseases. The major in vivo metabolites of paclitaxel have been identified, particularly the following hydroxylated paclitaxel metabolises A, B and C:

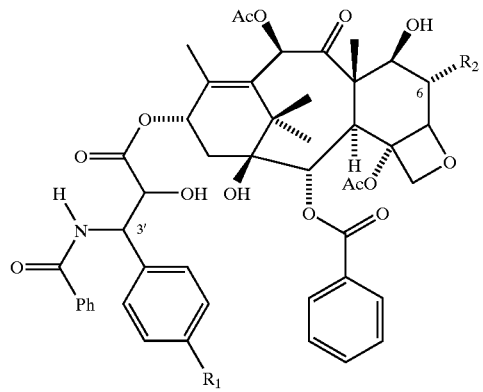

A: $R_1$—$H_1R_2$=OH; B: $R_1$=OH, $R_2$=H; C: $R_1$=OH, $R_2$=OH (Paclitaxel: $R_1$=H, $R_2$=H)

In certain in vitro tests metabolite B shown above (also referred to in the literature as metabolise M4) has been found to have a higher therapeutic index (ratio of toxic concentration level to effective concentration level) than paclitaxel in some human tumour cell lines. The invention possibly enables delivery of enhanced amounts of metabolite B and other active metabolites of paclitaxel to tumour sites because upoii oral administration all of the administered paclitaxel will pass through the liver and undergo metabolism by liver microsomes, yielding more of each metabolite in the systemic circulation than is achieved with IV administration.

An additional aspect of the invention relates to kits to be used in the treatment of mammalian patients suffering from conditions responsive to any pharmacologically active target agents whose oral absorption and bioavailability is increased by an enhancing agent. These kits include one or more oral dosage forms of at least one enhancing agent and one or more oral dosage forms of at least one target agent, or one or more dosage forms which comprise both.

By way of illustration, a kit of the invention may include one or more tablets, capsules, caplets, gelcaps or liquid formulations containing the bioenhancer of the present invention, and one or more tablets, capsules, caplets, gelcaps or liquid formulations containing paclitaxel in dosage amounts within the ranges described above. Such kits may be used in hospitals, clinics, physician's offices or in patients' homes to facilitate the co-administration of the enhancing and target agents. The kits should also include as an insert printed dosing information for the co-administration of the enhancing and target agents.

The subject kits may also include combinations of different enhancing agents and/or combinations of target agents. For example, a kit may include oral dosage forms 9,10-dihydro-5-methoxy-9-oxo-N-[4-[2-(1,2,3,4-tetrahydro-6,7-dimethoxy-2-isoquinolinyl)ethyl]phenyl]-4-acridinecarboxamide as enhancing agent, with paclitaxel alone as the target agent or with a combination of paclitaxel and another antitumour drug. The second target agent should be (like paclitaxel) a drug that exhibits poor oral bioavailability but with co-administration of enhancing agents can achieve therapeutically effective blood levels upon oral administration. The target agent may co-exist with the enhancing agent in the same dosage form or may be in a separate dosage form.
FIG. 1.

Comparison of paclitaxel concentration with time after oral administration of paclitaxel in combination with GF120918 compared to oral administration of paclitaxel on its own.

EXAMPLE 1

Materials and Methods for Animal Studies

Female FVB Wild-type mice, aged between 10 to 14 weeks and weighing between 20 to 30 g were used.
Drugs and Administration Route Paclitaxel (Taxol™) from, Bristol Myers Squibb was dissolved in vehicle consisting of Cremophor EL:Ethanol (1:1).(v/v) at a concentration of 6 mg/ML. Paclitaxel was given orally at a dose of 10 mg/kg. Oral drug administration was done by injection with a blunt needle via the oesophagus into the stomach.

9,10-dihydro-5-methoxy-9oxo-N-[4-[2-(1,2,3,4-tetrahydro-6,7,-dimethoxy-2-isoquinolinyl)ethyl]phenyl]-4-acridinecarboxamide (GF120918) (hydrochloride salt) from GlaxoWellcome was dissolved in vehicle consisting of 0.5% (w/v) hydroxypropylmethylcellulose (K15M Premium) with 1% (w/v) Tween 80 in Water for irrigation giving a final concentration of 2.5 mg/mL. GF120918 was administered orally at a dose of 25 mg/kg. Oral administration was done by injection with a blunt needle via the oesophagus into the stomach.
Preparation of StockVehicle and GF120918 Suspension Concentrated stock vehicle preparation for GF120918 (1L): weigh 10 g of hydroxypropylmethylcellulose into a suitable container . On a hot plate, heat approximately 500 g of water for irrigation to no less than 80° C. Stop heating the mixture and commence stirring with a magnetic stir bar and stir plate. Continue mixing and gradually add the hydroxypropylmethylcellulose . Leave stirring for at least 15 minutes to ensure dispersion. Continue stirring until the solution has cooled to approximately 30° C., then add 20 g of Tween 80 and mix thoroughly for approximately 5 to 10 minutes. Add sufficient water for irrigation to achieve a final weight of 1,000 g and mix. Dispense the HPMC solution into a suitable container and store at 2 to 80° C., protected from light.

2.2mg GF120918x/ml Suspension: Weigh 0.206 g of GF120918 into a suitable container and mix with sufficient water for irrigation to make a slurry. Transfer 37.5 mL of the measured concentrated stock vehicle to a graduated cylinder and add the GF120918 slurry on top of this concentrated stock vehicle. Rinse all the transfer vessels with water for irrigation and transfer to the graduated cylinder until a final volume of 75 mL is obtained. Mix by inversion for approximately 10 minutes to ensure that the test article is dispersed evenly throughout the suspension. Add additional water for irrigation if the meniscus of the preparation has fallen below 75 mL after mixing. Dispense the 75 mL of suspension into a labelled container and mix the suspension with a Polytron homogeniser for up to one minute. After mixing with the Polytron homogeniser, continue to mix the suspension with a magnetic stir bar and stir plate. Dispense the dose preparation into labelled amber containers. Store the dose preparation between 18 and 25° C., protected from light. The material should be mixed with a magnetic stir bar and stir plate at least 30 minutes before and during dosing the animals.
Test Groups The animals were divided into two test groups A and B.
Group A (control): consisted of a total of 42 animals. Paclitaxel was administered to the mice orally as described above . This group did not receive any GF120918, only vehicle. Blood samples were collected after 0.5, 1, 2, 3, 4, 6, and 8 hours by anaesthetising the animals using diethyl ether, fixation on their back, with their chest in an upright position, so that blood could be collected by heart punction using a 1 mL syringe filled with 10 µL of heparin solution as anticoagulant. The number of animals per sampling time point was 6. The blood samples were centrifuged in a Eppendorf microvial for 5 min at 1500 g. The supernatant plasma fraction was transferred to a clean vial and stored at −20° C. until analysis.

GroupB (test): consisted of 60 animals. Both Paclitaxel and GF120918 were administered to the mice orally as described above. Blood samples were collected as described for Group A after 0.5, 1, 2, 3, 4, 6, 8, 12, 16 and 24 hours with 6 animals per sampling time point.
Analytical Methods Analysis of paclitaxel levels in the plasma samples was performed using a validated HPLC methodology ((Bioanalytical report "Analysis of paclitaxel in human plasma by high performance liquid chromatography (HPLC) with UV detection" version 2.0, Approval dated: Apr. 1, 1996).
Results FIG. 1 clearly shows that compared to oral paclitaxel without GG120918 (control) the combination of paclitaxel with GF120918 (test) significantly increases the systemic exposure of wild mice to paclitaxel. More specifically in FIG. 1, GF120918 increases the AUC value 5 fold, and the plasma concentration of paclitaxel is increased 7 fold.

Previous experiments gave an AUC value of 710±100 for intravenously administered tpaclitaxel (without GF120918) giving an approximate increase of 60% bioavailability with oral paclitaxel in combination with GF120918.

What is claimed is:
1. A method of increasing oral bioavailability of paclitaxel or docetaxel upon oral administration to a mammalian patient, comprising: co-administration to the patient of enhanced effective amounts of oral paclitaxel or docetaxel and an oral bioenhancer which is 9,10-dihydro-5-methoxy-9-oxo-N-[4-[2-(1,2,3,4-tetrahydro-6,7,-dimethoxy-2-isoquinolinyl)ethyl]phenyl]-4-acridinecarboxamide.

* * * * *